United States Patent [19]

Narula et al.

[11] Patent Number: 5,179,222
[45] Date of Patent: Jan. 12, 1993

[54] PROCESS FOR PREPARING PHENYL BUTYRONITRILES AND PERFUMERY USE OF 2,2-DIMETHYL-4-PHENYL VALERONITRILE

[75] Inventors: Anubhav P. S. Narula, Hazlet; John J. De Virgilio, Freehold; William L. Schreiber, Jackson, all of N.J.

[73] Assignee: International Flavors & Fragrances Inc., New York, N.Y.

[21] Appl. No.: 858,536

[22] Filed: Mar. 27, 1992

Related U.S. Application Data

[62] Division of Ser. No. 759,155, Sep. 13, 1991, Pat. No. 5,143,899.

[51] Int. Cl.$^5$ .......................................... C07C 253/30
[52] U.S. Cl. .................................. 558/378; 558/388; 512/6
[58] Field of Search ........................................ 558/378

[56] References Cited

FOREIGN PATENT DOCUMENTS 894394 10/1953 Fed. Rep. of Germany ...... 558/378

OTHER PUBLICATIONS

Semmelhack, et al, J. Am. Chem. Soc., vol. 102, No. 21, (1980), pp. 6584–6586, (Title of Paper: "Arene-Metal Complexes in Organic Synthesis: Addition to Styrene-Type Ligands").

*Primary Examiner*—Joseph Paul Brust
*Attorney, Agent, or Firm*—Arthur L. Liberman

[57] ABSTRACT

Described is the use in imparting, augmenting or enhancing aromas to or in perfume compositions, colognes and perfumed articles by admixing therewith an aroma imparting, augmenting or enhancing quantity of 2,2-dimethyl-4-phenyl valeronitrile defined according to the structure:

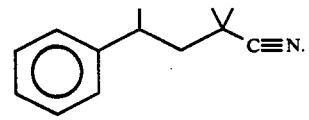

Also described herein is a process for preparing phenyl butyronitriles by reacting isobutyronitrile having the structure:

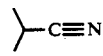

with a styrene derivative defined according to the structure:

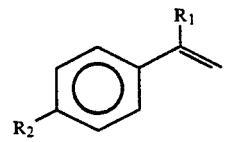

according to the reaction:

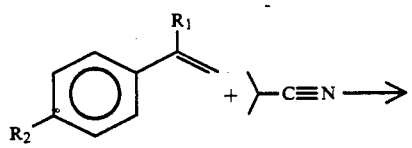

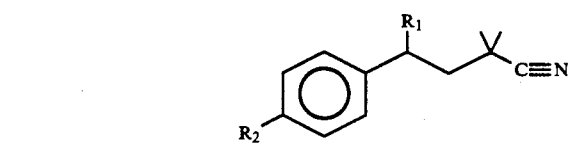

in the presence of a catalyst selected from the group consisting of sodium hydride and lithium diisopropyl amide having the structure:

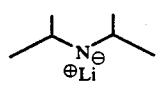

at a temperature in the range of from about 90° C. up to about 130° C. yielding more than about 65% by weight of product wherein $R_1$ and $R_2$ are the same or different and each represents hydrogen or methyl.

4 Claims, 6 Drawing Sheets

GLC PROFILE FOR EXAMPLE III.

NMR SPECTRUM FOR EXAMPLE III

FIG.2-A
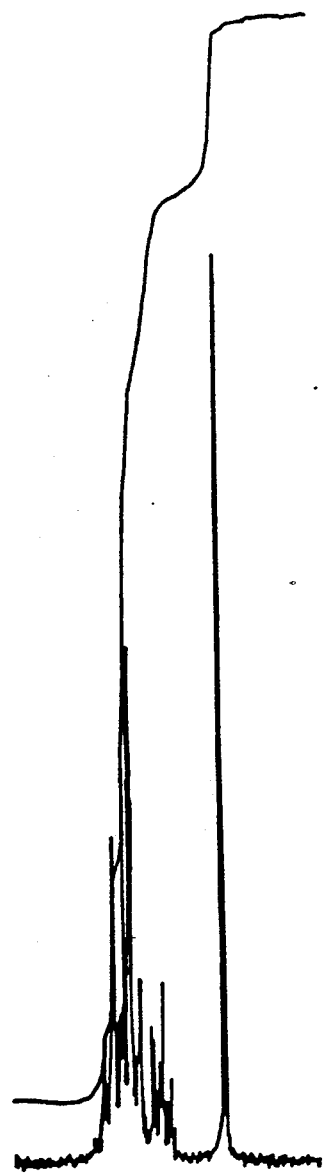
7.4 7.2 7.0 6.8
PPM
FIG.2-B
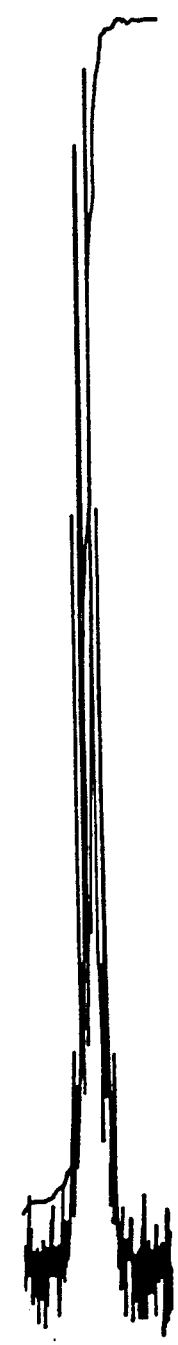
3.0
PPM

FIG. 2-C
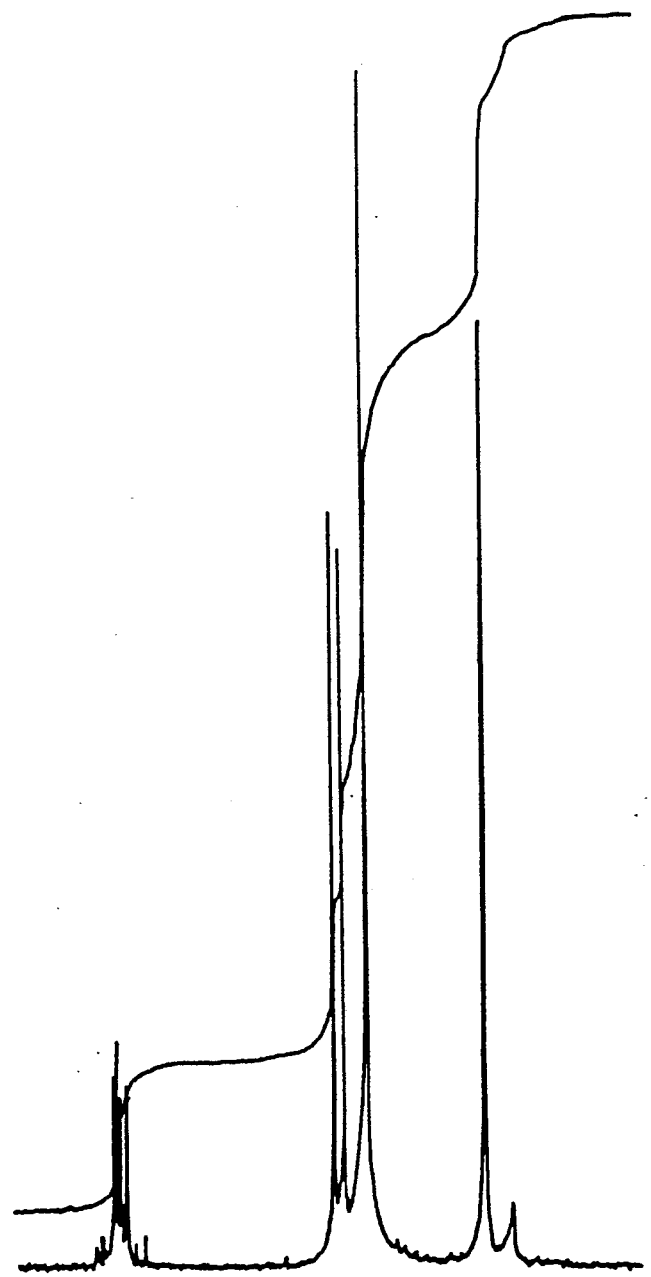
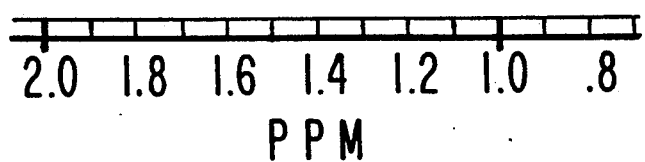

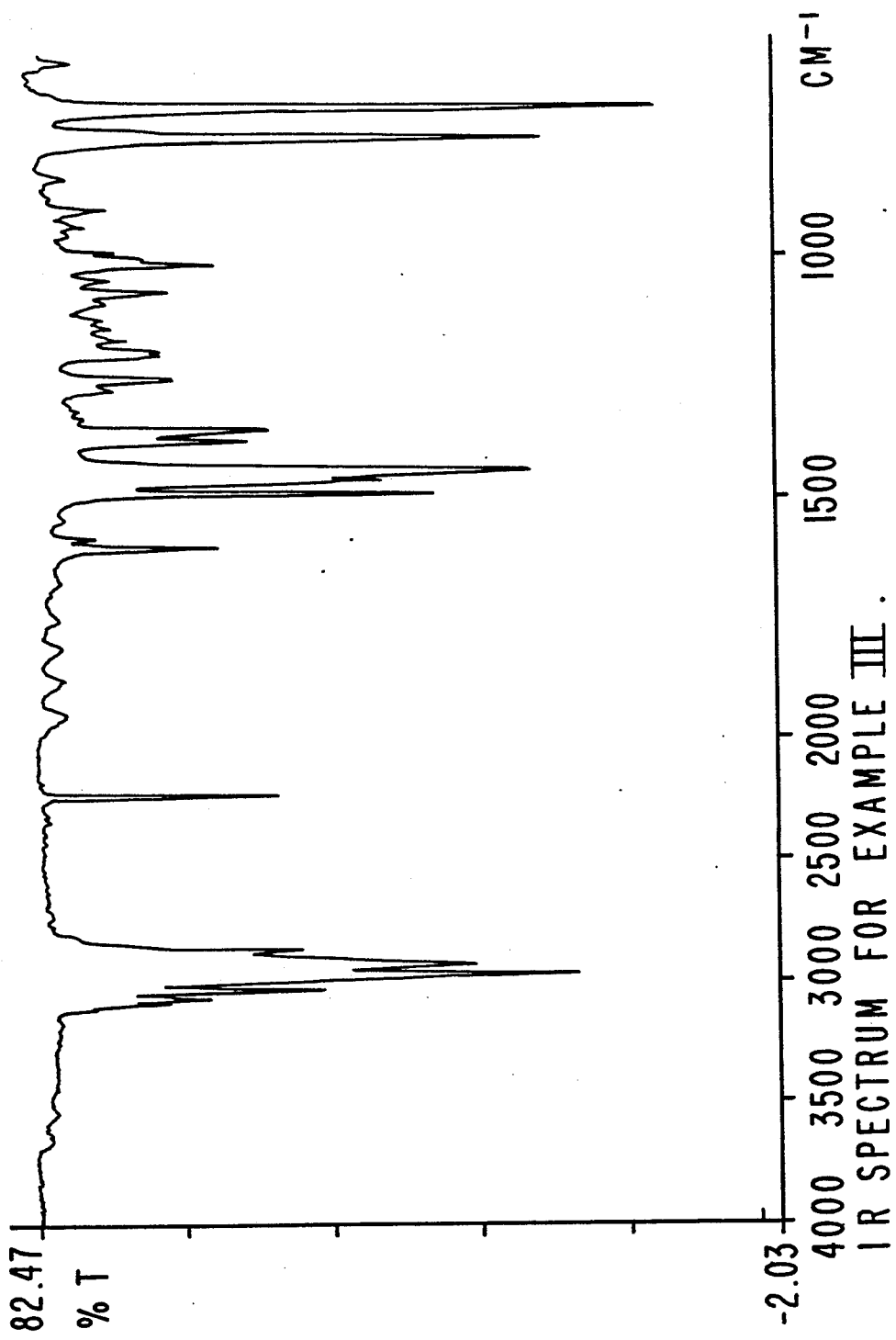
FIG.3 IR SPECTRUM FOR EXAMPLE III.

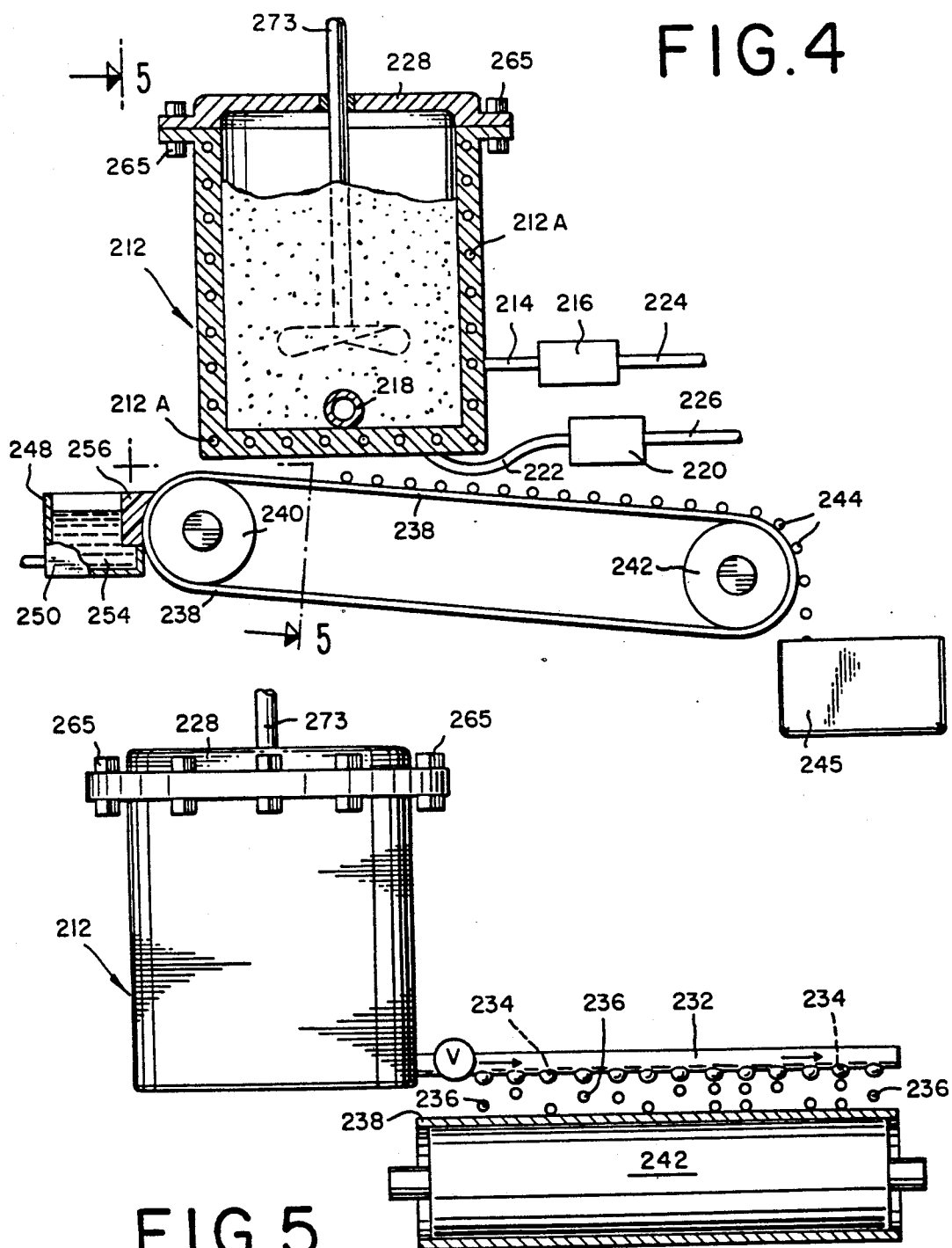

PROCESS FOR PREPARING PHENYL BUTYRONITRILES AND PERFUMERY USE OF 2,2-DIMETHYL-4-PHENYL VALERONITRILE

This is a divisional of Ser. No. 759,155, filed Sep. 31, 1991, now U.S. Pat. No. 5,143,899.

BACKGROUND OF THE INVENTION

This invention relates to phenyl butyronitriles, methods of preparing same and uses thereof in augmenting, imparting or enhancing aromas in or to perfume compositions, perfumed articles and/or colognes.

There has been considerable work performed relating to substances which can be used to impart (modify, augment or enhance) fragrances to (or in) various consumable materials. These substances are used to diminish the use of natural materials, some of which may be in short supply and to provide more uniform properties in the finished product.

Long-lasting substantive vetivert, peppery, grapefruit and Bergamot aromas, with vetivert, peppery and Bergamot topnotes are highly desirable in several types of perfume compositions, perfumed articles and colognes (e.g., piney fragrances).

The perfume uses of nitrile-containing derivatives which also contain phenyl moieties are well known in the prior art. Thus, the compound having the structure:

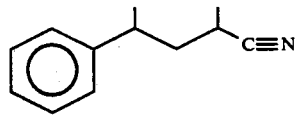

is shown to be useful in perfumery in U.S. Letters Pat. No. 4,837,351 issued on Jun. 6, 1989 wherein it is indicated that it has a powerful fresh, fruity, floral odor note accompanied by a citrus, green topnote Furthermore, U.S. Letters Pat. No. 3,325,369 discloses the use of cinnamonitrile as a material useful in augmenting or enhancing the aroma of perfume compositions.

Other nitriles containing gem-dimethyl moieties "alpha" to the cyanide moiety are disclosed in Blumenthal, et al, U.S. Pat. No. 3,168,550 issued on Feb. 2, 1965.

Nothing in the prior art discloses the use in perfumery of the 2,2-dimethyl-4 TM phenyl valeronitrile of our invention.

Furthermore, preparation of phenyl butyronitriles are taught in the prior art to be rather complex and costly Thus, the 2,2-dimethyl-4-phenyl valeronitrile of our invention is shown to be prepared according to the reaction:

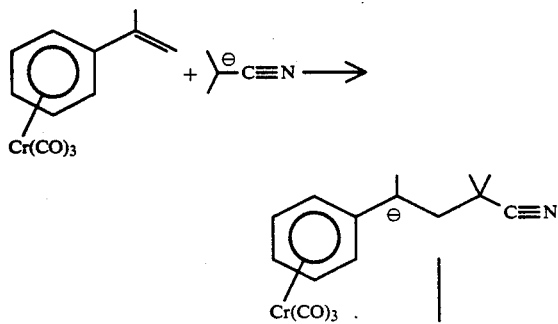

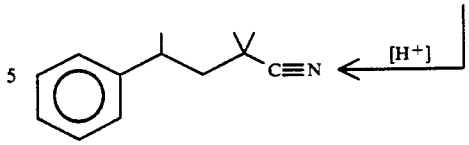

using a chromium carbonyl complex by Semmelhack, et al, J.Am.Chem.Soc., 1980, 102, 6584–6586.

Nothing in the prior art indicates the commercially useful process of our invention shown by the reaction:

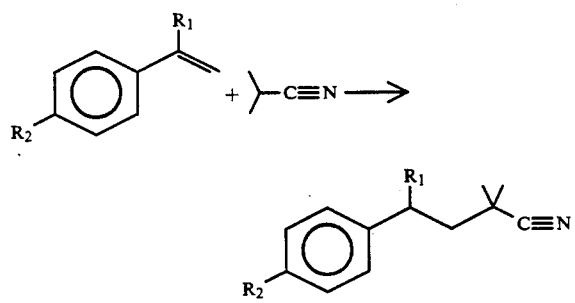

taking place in the presence of a sodium hydride or lithium diisopropyl amide catalyst at temperatures in the range of from about 90° C. up to about 130° C.

Furthermore, considerable difficulties have heretofore been encountered in using compounded hypochlorite bleach or sterilizing solutions with perfumed oils so that a stable long-lasting, single phase commercially feasible bleach or sterilizing solution has been difficult to obtain, particularly wherein the desired aroma of the article bleached or sterilized (e.g., clothing) has a pleasant and stable and consistent aroma on drying (and not the usual "hypochlorite-bleached-article" aroma). The problem has been defined in United Kingdom Patent Specification No. 886,084 published on Jan. 3, 1962 wherein it is stated that a stable "dispersion" of hypochlorite-resistant perfume in aqueous solutions of hypochlorites was formulated. United Kingdom Patent Specification No. 886,084 discloses the preparation of an aqueous "solution" of a hypochlorite containing a hypochlorite resistant perfume and a surface active quaterary ammonium compound of the betaine type soluble in the hypochlorite solution. Such ammonium compounds have the generic structure:

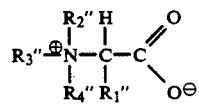

wherein each of $R_1''$, $R_2''$, $R_3''$ and $R_4''$ are alkyl. One of the features of the perfumed solutions produced in accordance with said United Kingdom Patent Specification No. 886,084 is indicated to be that the solution exhibits foaming properties Another feature of United Kingdom Patent Specification No. 886,084 is stated to be that the perfumed solutions covered by the patent are found to be clear and homogeneous after eight weeks of storage at room temperature. Nevertheless, betaines such as "Ambiteric D" as are discussed therein are not so broadly useful when used in concentrations of from 0.15% up to 4.0% (based on total weight of bleach or sterilizing solution) as to have the ability to be used in conjunction with perfume oils which should be incorporated into thickened, high viscous hypochlorite bleaches or sterilizers having excellent surface tension properties so that long-lasting stable soluble single phase thickened perfumed aqueous alkali metal hypochlorite bleach or sterilizing solutions having longlasting pleasant stable aromas are obtained, particularly where the quantity of perfume oil in the bleach or sterilizing substance is at levels of between 0.02% and 0.8% by weight of the total bleach or sterilizing solution. The need for such aromas (e.g., "citrusy") to be present in such bleach or sterilizing solutions exists so that the disagreeable characteristic "hypochlorite" aroma is substantially eliminated from aromas of the end product to which the bleach or sterilizing solution is applied; particularly on dry-out, as well as from the aroma of the hands of the user when they are in direct contact with such bleach or sterilizing solutions.

U.S. Pat. No. 3,560,389 also discloses the feasibility of using perfume oils in hypochlorite bleaches or sterilizers at column 3, lines 37-40 but the disclosure is limited to inclusion of various detergents in addition to amine oxides, such as lithium lauryl sulfate and sodium lauryl ether sulfate and/or is further limited to include hydrotropes such as sodium xylene sulfonate in addition to the amine oxide. Exclusion of such hydrotropes and detergents additional to the amine oxides and diphenyl oxide derivatives of our invention is desirable not only to cause the phenyl butyronitriles of our invention to function properly, but also from an ecological standpoint.

European Chemical News, Volume 13, Jan. 18, 1968, sets forth a synopsis of South African Patent No. 67/4667 which corresponds to U.S. Pat. No. 3,560,389, but the reference also states at page 42:

"Alternatively, a detergent with bleaching or bacteriocidal properties can be formulated. Perfuming bleaching solutions is now possible."

Neither the South African nor the United States Patents, however, indicate the advantages and usefulness of limiting the detergents either to (a) compounds having the generic structure:

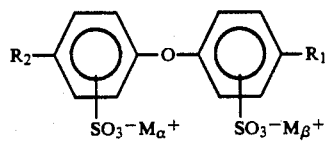

wherein at least one of $R_1$ and $R_2$ represents $C_{10}$–$C_{12}$ straight chain or branched chain alkyl and when one of $R_1$ or $R_2$ is $C_{10}$–$C_{12}$ branched or straight chain alkyl, the other of $R_1$ or $R_2$ is pH-adjusted hydrogen and wherein $M_{60}$ and $M_{62}$ are the same or different and each represents alkyl metal which may be sodium, lithium or potassium, or (b) to mixtures of compounds having the structure:

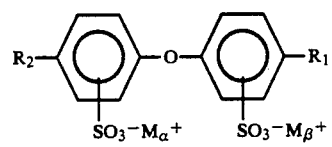

with at least one amine oxide defined according to the structure:

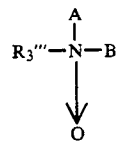

of excluding from the formulation a hydrotrope or of specifying the nature of the perfume oil useful in the perfumed bleach or sterilizing solution (wherein A and B are each separately methyl or taken together, complete a morpholino ring and wherein $R_3'''$ is straight chain alkyl having from 11 up to 13 carbon atoms).

U.S. Pat. No. 3,876,551 in attempting to solve the foregoing problem discloses a stable single phase aqueous alkali metal hypochlorite liquid perfume bleach or sterilizing composition comprising an aqueous mixture of (1) an amine oxide composition consisting essentially of at least one morpholino and/or dimethyl ($C_{11}$–$C_{13}$ straight chain alkyl) amine oxide in an amount greater than 55% of said amine oxide composition, (2) at least one alkali metal hydroxide, (3) at least one alkali metal hypochlorite, and (4) a perfume oil compatible with the mixture capable of imparting a "woody" or a "floral" or a "clean fresh" or a "citrusy" note to the bleach or sterilizing composition; the mixture having a pH in the range of from 12 to 13.5 and the mixture excluding hydrotropes as well as all surfactants except the amine oxide. U.S. Pat. No. 3,876,551 also attempts to solve the foregoing problem by disclosing a process for producing the above TM named mixture comprising the steps of combining an amide oxide composition consisting essentially of one or more morpholino and/or dimethyl $C_{11}$–$C_{13}$ straight chain alkyl amine oxide(s) with the perfumed oil to form an amine oxide-perfume oil premix; admixing the amine oxide-perfumed oil premix with an aqueous alkali metal hypochlorite solution, and combining an alkali metal hydroxide with the solution whereby the final pH of the mixture is from 12 up to 13 5. In a further effort to solve the foregoing problem U.S. Pat. No. 3,876,551 also discloses adjustment of the pH of the aqueous metal hypochlorite solution initially to the range of 12-13.5 and then combining the resulting aqueous hypochlorite solution with the aforementioned premix. The resulting composition is indicated to cause products to which said composition is applied to have eliminated therefrom the disagreeable characteristics "hypochlorite" aroma and instead to have a "clean fresh" or "floral" or "woody" or citrusy" aroma to be imparted to the treated products. In addition, it is stated that the hands of the individual user after using and being in direct contact with the hypochlorite composition will not have the disagreeable characteristics "hypochlorite" aroma but instead will have a pleasant "clean fresh" or "floral" or "woody" or "citrusy" aroma.

The disadvantage of the system of U.S. Pat. No. 3,876,551, however, concerns (a) the inability to use a thickener in the system whereby the resulting liquid has a viscosity of 5-25 centipoises at 20°-40° C. and (b) the relative chemical stability and substantive stability of the perfume oil and of the single liquid phase system Nothing in U.S. Pat. No. 3,876,551 indicates such a high degree of stabilities of the perfume-hypochlorite system as exists in the system of the present invention; wherein there is also included a thickener. Indeed, the stabilities using the system of the instant invention are far greater even at levels as low as 3% hypochlorite and are also relatively stable (from a standpoint of chemical stability of perfume oil, substantive stability of perfume oil and phase separation stability taken in combination with one another) at levels of as high as 10% hypochlorite in aqueous solution. Thus, the instant system gives rise to unexpected, unobvious and advantageous properties over the system taught in the prior art.

Furthermore, nothing in the prior art including the teaching of U.S. Pat. No. 3,876,551 states either explicitly or implicitly the compatability of a thickener in the instant system, such as sodium palmitate, sodium stearate, potassium, palmitate, potassium stearate, lithium palmitate, lithium stearate, lithium laurate, potassium laurate or sodium laurate whereby a stable gel (as opposed to a liquid) phase perfumed hypochlorite system or perfumed oil stabilizer emulsifier system "premix" may be produced.

The combination of the compound group having the structure:

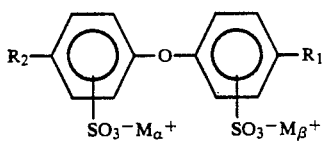

(wherein $R_1$, $R_2$, $M_\alpha$ and $M_\beta$ are defined, supra) with perfume and hypochlorite bleach in general, is set forth in the Kao Soap Company, Japanese Patent. No. 25514/79 filed on Nov. 2, 1973 and opened for public inspection on Jun. 19, 1975. Thus, on page 2, at column 4, line 15, the compound:

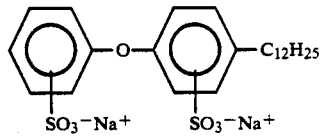

is disclosed for use in conjunction with the perfumed hypochlorite bleaches. The claim of the Kao Soap Patent is as follows:

Claim: An aromatic liquid bleaching composition containing, as active ingredient, sodium hypochlorite, which comprises one or more of simple perfumes or compounded perfumes selected from the group consisting of anisole, benzophenone, benzylphenyl ether, bromelia, cedrenyl acetate, p-tertiary butylcyclohexanol, di-methylbenzylcarbinyl acetate, dihydroterpinyl acetate, diphenyl oxide, dimethylbenzylcarbinol, dimethylphenyl-carbinol, dihydroterpineol, fenchyl acetate, fenchyl alcohol, p-methyldimethylbenzylcarbinol, methylphenylcarbinyl acetate, methyl-n-valerate, muskmoskene, muscarone, methylamyl ketone, phenylethyldimethylcarbinyl acetate, rose phenone, styrallyl propionate, tetra-hydromuguol, tetra-hydromuguyl acetate, tetra-hydrolinalool, tetra-hydrolinalyl acetate, verool, velveton, verdox, coniferan and yarayara, and a surface solution of sodium hypochlorite.

Furthermore, the use of such compounds as those having the structure:

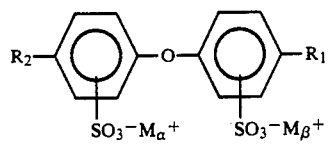

(wherein $R_1$, $R_2$, $M_\alpha$ and $M_\beta$ have been previously defined) with hypochlorite bleaches documented in the brochure of Dow Chemical entitled "DOWFAX® Surfactants" and is covered in the Dow Chemical Company U.S. Pat. No. 3,172,861 issued on Mar. 9, 1965.

The 2,2-dimethyl-4-phenyl valeronitrile of our invention is unique insofar as the aforementioned systems are concerned for use in hypochlorite bleaches. Nothing in the prior art discloses organic compounds having a structure even remotely similar to the 2,2-dimethyl-4-phenyl valeronitrile of our invention for use as a stable aroma imparting, augmenting or enhancing agent in hypochlorite bleaches.

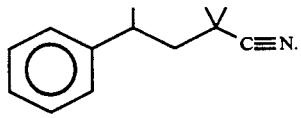

Figure 2:
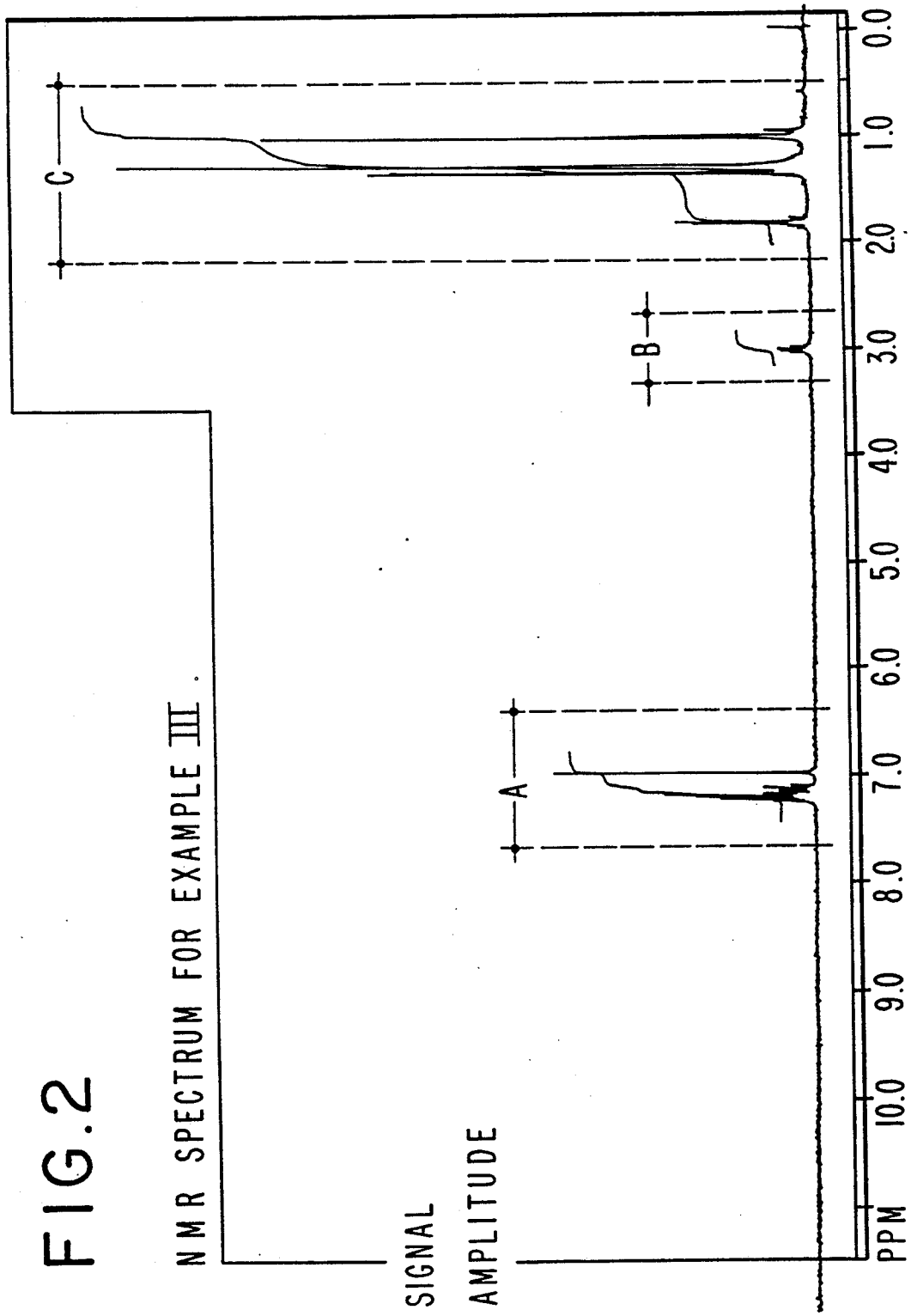

FIG. 2 is the NMR spectrum for the compound having the structure:

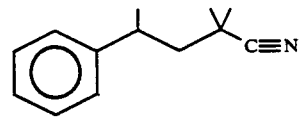

prepared according to Example III.

FIGS. 2A, 2B and 2C are detailed sections indicated by "A", "B" and "C" on the NMR spectrum of FIG. 2.

FIG. 3 is the infra-red spectrum for the compound having the structure:

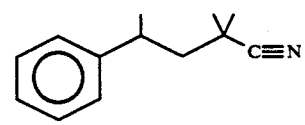

prepared according to Example III.

FIG. 4 represents a cut-away side elevation view of apparatus used in forming perfumed polymers which contain imbedded therein the 2,2-dimethyl-4-phenyl valeronitrile of our invention.

FIG. 5 is a front view of the apparatus of FIG. 4 looking in the direction of the arrows.

DETAILED DESCRIPTION OF THE DRAWINGS

Figure 1:
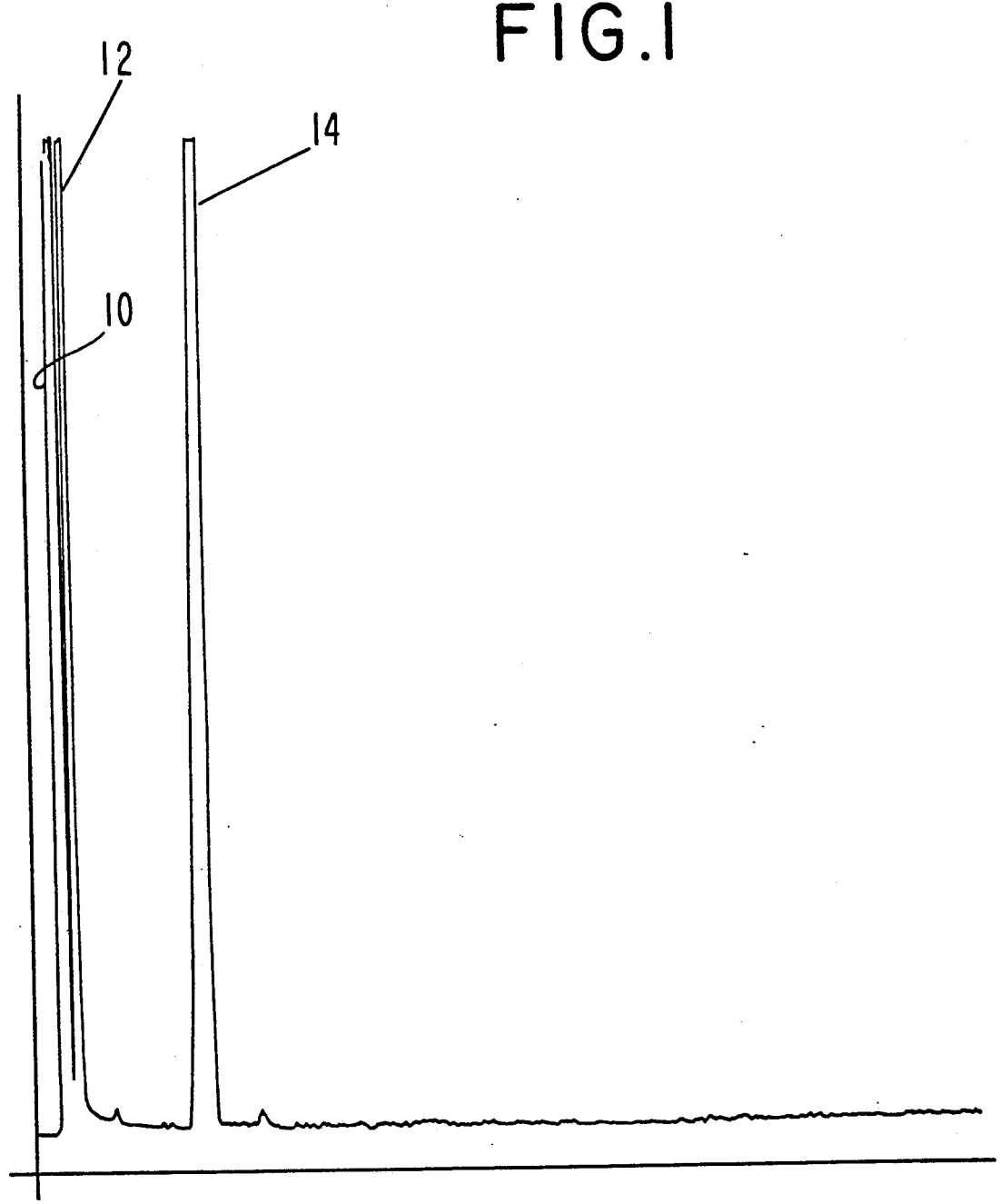
FIG. 1 is the GLC profile for the reaction product of Example III containing the compound having the structure.

FIG. 1 is the GLC profile for the crude reaction product of Example III. The peak indicated by reference numeral 10 is the peak for the starting material, isobutyronitrile, having the structure:

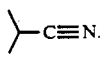

The peak indicated by reference numeral 12 is the peak for the alpha-methyl styrene starting material having the structure:

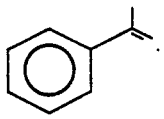

The peak indicated by reference numeral 14 is the peak for the reaction product having the structure:

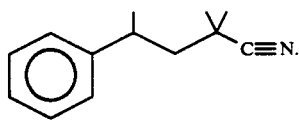

Referring to FIGS. 4 and 5, there is provided a process for forming scented polymer elements (wherein the polymer may be a thermoplastic polymer such as low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles which may be perfumed (and, further, which may be exposed to chlorine bleaches). This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring to FIGS. 4 and 5, in particular, the apparatus used in producing such elements comprises a device for forming the polymer containing the perfume, e.g., polyethylene or polyethylene-polyvinyl acetate or mixtures of same or polypropylene, which comprises a vat or container 212 into which the polymer taken alone or in admixture with other copolymers and the perfuming substance which is at least the 2,2-dimethyl-4-phenyl valeronitrile of our invention and other compatible perfumes is placed. The container is closed by means of an air-tight lid 228 and clamped to the container by bolts 265. A stirrer 273 traverses the lid or cover 228 in an air-tight manner and is rotatable in a suitable manner. A surrounding cylinder 212A having heating coils which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90–100 sayboldt seconds. The heater 218 is operated to maintain the upper portion of the container 212 within a temperature range of, for example, 220°–270° C. in the case of low density polyethylene. The bottom portion of the container 212 is heated by means of heating coils 212A regulated through the control 220 connected thereto through a connecting wire 222 to maintain the lower portion of the container 212 within a temperature range of 220°–270° C.

Thus, the polymer or mixture of polymers added to the container 212 is heated from 10–12 hours, whereafter the perfume composition or perfume material which contains the 2,2-dimethyl-4-phenyl valeronitrile of our invention is quickly added to the melt. Generally, about 10–45 percent by weight of the resulting mixture of the perfumery substance is added to the polymer.

After the perfume material is added to the container 212, the mixture is stirred for a few minutes, for example, 5–15 minutes and maintained within the temperature ranges indicated previously by the heating coil 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer in intimate admixture with the 2,2-dimethyl-4-phenyl valeronitrile of our invention and one or more other substances, will continuously drop through the orifices 234 downwardly from the conduit 232. During this time, the temperature of the polymer intimately admixed with the perfumery substance in the container 212 is accurately controlled so that a temperature in a range of from about 240°–250° C., for example, (in the case of low density polyethylene) will exist in the conduit 232. The regulation of the temperature through the controls 216 and 220 is essential in order to insure the temperature balance to provide for the continuous dripping or dropping of molten polymer intimately admixed with the perfume substance which is all of or which contains the 2,2-dimethyl-4-phenyl valeronitrile of our invention, through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instanteously and fall off the end of the conveyor 238 into a container 250 which is advantageously filled with water or some other suitable cooling liquid to insure the rapid cooling of each of the pellets 244. The pellets 244 are then collected from the container 250 and utilized for the formation of functional products, e.g., garbage bags and the like.

THE INVENTION

The present invention provides processes for preparing phenyl butyronitriles as well as the use of one of these phenyl butyronitriles in augmenting or enhancing or imparting aroma to or in perfume compositions, perfumed articles and colognes, to wit: 2,2-dimethyl-4-phenyl valeronitrile.

The process for preparing phenyl butyronitriles encompasses processes for preparing the compounds having the structures:

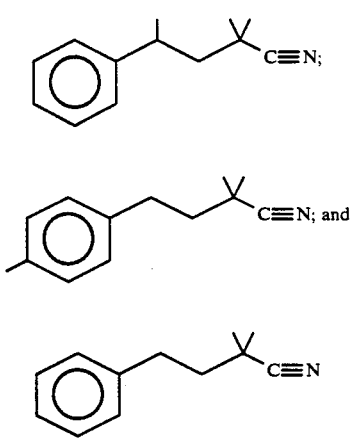

each of which has a use in augmenting or enhancing the aroma of perfume compositions, colognes and perfumed articles, including but not limited to perfumed polymers, cosmetic powders, anionic, cationic, nonionic or zwitterionic detergents, fabric softener compositions, fabric softener articles including drier-added fabric softener articles (e.g., BOUNCE® marketed by the Procter & Gamble Company of Cincinnati, Ohio).

The 2,2-dimethyl-4-phenyl valeronitrile of our invention is capable of imparting, augmenting or enhancing vetivert, peppery, grapefruit and Bergamot aromas, with vetivert, peppery and Bergamot topnotes to perfume compositions, colognes and perfumed articles including soaps, bleaches, anionic, cationic, nonionic or zwitterionic detergents, fabric softener articles and other perfumed articles.

The process of our invention involves reaction of isobutyronitrile having the structure:

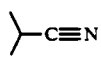

with at least one of the compounds defined according the generic structure:

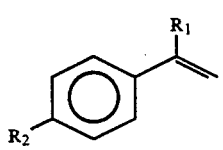

(wherein $R_1$ and $R_2$ are the same or different and each represents hydrogen or methyl) at a temperature in the range of 90°-130° C. in the presence of a catalyst which may be either sodium hydride or diisopropyl amide having the structure:

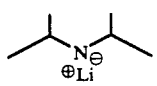

according to the reaction:

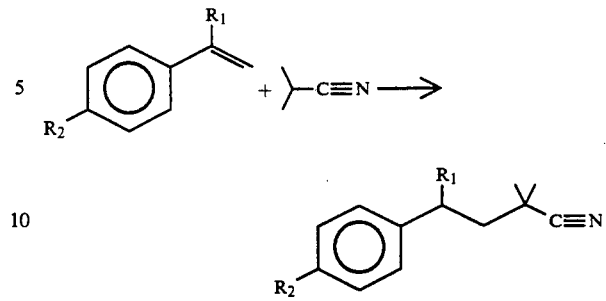

Preferably the reaction takes place at atmospheric pressures. The mole ratio of reactants is preferably about 1:1 with an excess of isobutyronitrile (e.g., 50% molar excess being preferred). The mole percentage of catalyst, e.g., sodium hydride or lithium diisopropyl amide in the reaction may vary from about 5% up to about 20% with a preferred mole percentage range of catalyst varying between 6 and 10%.

The following table sets forth the reactants, reaction products and yields for the process of our invention:

TABLE I

| Reactants | Reaction Product | Yield of Product |
|---|---|---|
| Compounds having the structures: ⟩—C≡N and ⌬⟩⟨ | Compound having the structure: ⌬⟩⟨⟨C≡N prepared according to Example I. | 74% |
| Compounds having the structures: ⌬⟩⟨ and ⟩—C≡N | Compound having the structure: ⌬⟩⟨⟨C≡N prepared according to Example II. | 65% |
| Compounds having the structures: ⌬⟩⟨ and ⟩—C≡N | Compound having the structure: ⌬⟩⟨⟨C≡N prepared according to Example III. | 88% |

Although the compounds defined according to the generic structure:

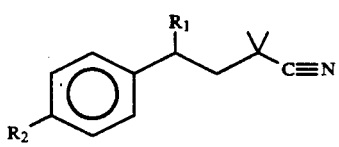

wherein, $R_1$ and $R_2$ are the same or different hydrogen or methyl are all useful in augmenting, imparting or enhancing an aroma in or to perfume compositions, perfumed articles and colognes, the compound having the structure:

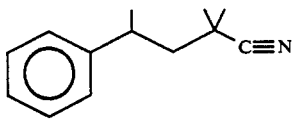

has unexpected, unobvious and advantageous properties when compared to the compounds of the prior art.

The compound having the structure.

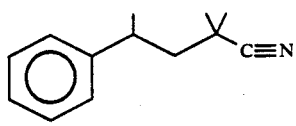

has an intense vetivert, peppery, grapefruit and Bergamot aroma, with vetivert, peppery and Bergamot topnots. On a scale of 1 to 10, the quality of the compound having the structure:

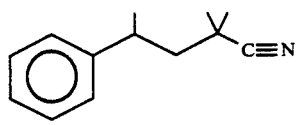

has a rating of 10; the intensity of the compound having the structure:

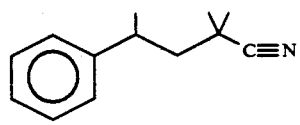

has a rating of "9" and the skin substantivity of the compound having the structure:

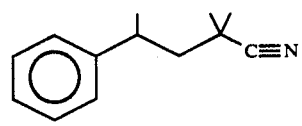

has a rating of "10". On the other hand, the "closest" compound of the prior art, the compound having the structure:

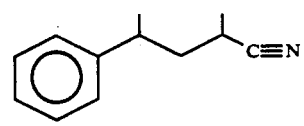

prepared according to the process of Torihara, et al, U.S. Letters Pat. No. 4,837,351 issued on Jun. 6, 1989 has been found to have a vetivert and grapefruit aroma with very metallic, dirty feeling vetivert and grapefruit topnotes. On a scale of 1 to 10 it has a quality of "2". On a scale of 1 to 10, it has an intensity of "6" and on a scale of 1–10, it has a skin substantivity of "8".

The 2,2-dimethy1-4-phenyl valeronitrile of our invention and one or more auxiliary perfume ingredients, including, for example, hydrocarbons, alcohols, ketones, aldehydes, nitriles (other than the nitrile of our invention), esters, lactones, ethers, hydrocarbons, synthetic essential oils and natural essential oils may be admixed so that the combined odors of the individual components produce a pleasant and desired fragrance particularly and preferably in the "pine fragrance" area Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute to their particular olfactory characteristics, however, the overall sensory effect of the perfume composition will be at least the sum total of the effects of each of the ingredients. Thus, the 2,2 TM dimethyl-4-phenyl valeronitrile of our invention can be used to alter, modify or enhance the aroma characteristics of a perfume composition, for example, by utilizing or moderating the olfactory reaction contributed by another ingredient in the composition.

The amount of 2,2 TM dimethyl-4-phenyl valeronitrile of our invention which will be effective in perfume compositions as well as in perfumed articles and colognes depends upon many factors, including the other ingredients, their amounts and the effects which are desired. It has been found that perfume compositions containing as little as 0.05% of the 2,2-di-methyl-4-phenyl valeronitrile of our invention can be used to impart vetivert, peppery, grapefruit and Bergamot aromas, with vetivert, peppery and Bergamot topnotes to soaps, cosmetics, detergents (including anionic, cationic, nonionic or zwitterionic solid or liquid detergents) or other products. The amount employed can range up to 70% of the fragrance components and will depend upon considerations of cost, nature of the end product, the effects desired on the finished product and the particular fragrance sought.

The 2,2-dimethyl-4-phenyl valeronitrile of our invention is useful (taken alone or together with other ingredients in perfume compositions), in detergents and soaps, space odorants and deodorants, perfumes, colognes, toilet water, bath preparations such as lacquers, brilliantines, pomades and shampoos; cosmetic preparations such as creams, deodorants, hand lotions and sun screens; powders, such as talcs, dusting powders, face powders and the like.

As little as 0.7% of the 2,2-dimethyl-4-phenyl valeronitrile of our invention will suffice to impart an intense and substantive vetivert, peppery, grapefruit and Bergamot aroma, with vetivert, peppery and Bergamot topnotes to pine perfume formulations. Generally, no more than 5% of the 2,2-dimethyl-4-phenyl valeronitrile of our invention based on the ultimate end product is required to be used "as is" or in the perfume composition.

Furthermore, as little as 0.25% of the 2,2-dimethyl-4-phenyl valeronitrile of our invention will suffice to impart such aroma to perfumed articles per se, whether in the presence of other perfume materials or whether used by itself. Thus, the range of use of the 2,2-dimethyl-4-phenyl valeronitrile of our invention in perfumed articles may vary from about 0.25% up to about 5% by weight based on the total weight of the perfumed article.

In addition, the perfume composition or fragrance compositions of our invention can contain a vehicle, or carrier of the 2,2-dimethyl-4-phenyl valeronitrile of our invention. The vehicle can be a liquid such as a non-toxic alcohol, e.g., ethanol, a non-toxic glycol, e.g., propylene glycol or the like. The carrier can also be an absorbent solid, such as a gum (e.g., gum arabic), or components for encapsulating the composition by means of coacervation (such as gelatin).

It will thus be apparent that the 2,2-dimethyl-4-phenyl valeronitrile of our invention can be utilized to alter, modify or enhance the aroma of perfume compositions, colognes or perfumed articles.

Furthermore, several processes may be used in order to produce a thickened, highly viscous hypochlorite bleaching or sterlizing solution whereby the desired aroma profiles are imparted to the articles treated with said hypochlorite solutions.

Thus, for example, the 2,2-dimethyl-4-phenyl valeronitrile of our invention may be premixed with the diphenyl oxide derivative or diphenyl oxide derivative-amine oxide solubilizer-stabilizer (having the structures, respectively:

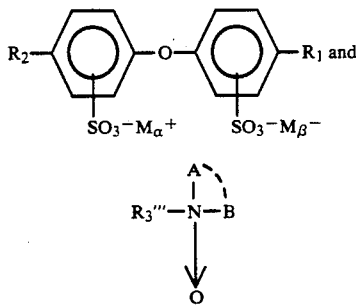

and the resulting 2,2-dimethyl-4-phenyl valeronitrile-containing premix is then mixed with the hypochlorite bleaching or sterilizing solution with stirring. Immediately after such addition, an aqueous alkali metal hydroxide solution is added to the mixture to bring the pH to the range of 11-14.0. A pH of less than 11 is not desired since it is difficult to achieve a single phase stable system at low pH's. A pH higher than 14.0 will also create a system which (1) is unnecessarily corrosive; (2) will narrow the range of perfume oils useable (in conjunction with the 2,2-dimethyl-4-phenyl valeronitrile of our invention of the system and (3) will limit the particular ingredients useable in such perfume oils in conjunction with the 2,2-dimethyl-4-phenyl valeronitrile . On the other hand, if for example, the 2,2-dimethyl-4-phenyl valeronitrile is used alone or further in combination with (i) diisoamylene epoxides; (ii) diisoamylenes as described in application for U. S. Letters Pat., Ser. No. 188,576 filed on Oct. 9, 1980; now U.S. Letters Pat. No. 4,303,555 issued on Dec. 1, 1981 or (iii) acyl diisoamylene derivatives described in application for U.S. Letters Pat., Ser. No. 184,132 filed on Sep. 4, 1980, now U.S. Letters Pat. No. 4,321,255 issued on Mar. 23, 1982 and/or (iv) ketal derivatives of acyl diisoamylene derivatives described in application for U.S. Letters Patent, Ser. No. 212,993 filed on Dec. 4, 1980, now U.S. Letters Pat. No. 4,315,952 issued on Feb. 16, 1982, a pH of about 14.0 and even slightly higher (e.g., 14.1) is acceptable.

The aqueous alkali metal hydroxide can be added to the aqueous alkali metal hypochlorite solution before adding the diphenyl oxide derivatives (taken alone or in conjunction with the amine oxide) or the 2,2-dimethyl-4-phenyl valeronitrile with other materials such as diisoamylene epoxides. Indeed, the ingredients the 2,2-dimethyl-4-phenyl valeronitrile; the alkali metal hydroxide and the diphenyl oxide derivative or diphenyl oxide derivative-amine oxide composition (having the structures, respectively:

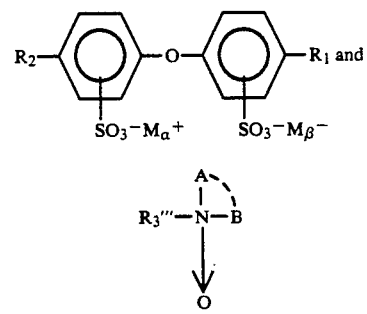

may be added or admixed in any order which is convenient to the formulator.

The alkali metal hypochlorites preferred in the practice of our invention are: sodium hypochlorite, potassium hypochlorite and lithium hypochlorite or mixtures of same. The alkali metal hypochlorites preferred in the practice of this invention are: lithium hydroxide, potassium hydorxide and sodium hydroxide, or, if desired, mixtures of such hydroxides.

The temperature at which the composition of our invention remains both-substantially stable and commercially useful for the purposes set forth herein (that is, remains as a clear single aqueous or gel phase) and retains (1) the desired properties inherent in the known bleaching and sterilizing uses of aqueous alkali metal hypochlorite liquid or gel solutions, and (2) the properties imparted thereto as a result of the use of the 2,2-dimethyl-4-phenyl valeronitrile which impart to articles previously subjected to the aqueous alkali metal hypochlorite gel or liquid solutions a desired aroma profile, varies from approximately 20° F. up to approximately 120° F. At temperatures below 20° F. a two-phase system usually occurs and at temperatures higher than 120° F. the bleaching or sterilizing efficiency of the compositions of our invention is diminished at an excessive rate.

When it is desired to (1) initially form the $C_{10}$-$C_{12}$ straight chain or branched chain diphenyl oxide alkali metal sulfonate or diphenyl oxide derivative-amine oxide premix; (2) then combine the resulting premix with an alkali metal hypochlorite solution; (3) then add the thickening agent and then (4) adjust the pH of the resulting solution to the range of 11-14.0, then the temperature of mixing ranges which are considered to be within the scope of this invention are as follows:

(a) Formation of the diphenyl oxide derivative or diphenyl oxide-amine oxide-2,2-dimethyl-4-phenyl valero nitrile premix..................... 20° F.-150° F.

(b) Mixing the premix with aqueous alkali metal hypochlorite solution followed by thickening agent .... 20° F.-120° F.

(c) Adjustment of pH of the solution to the range of 11-14.0 using aqueous alkali metal hydroxide solution.......................... 20° F.-120° F.

In any event, whenever a mixing unit operation involves the aqueous alkali metal hypochlorite solution, the temperature of mixing is limited to the range of 20° F. -120° F. Where the mixing unit operation involves the mixing of 2,2-dimethyl-4-phenyl valeronitrile, the upper bound of the temperature range is limited by the stability of the 2,2-dimethyl-4-phenyl valeronitrile useable in the practice of our invention; and the lower bound of said temperature range is limited by the least temperature where a single liquid phase or gel phase including the 2,2-dimethyl-4-phenyl valeronitrile or other ingredients admixed therewith will exist. Where a unit mixing operation of the process of our invention involves the mixing of one or more diphenyl oxide derivatives having the generic structure:

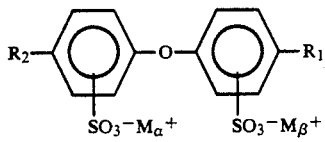

taken alone or taken together with one or more amine oxides having the generic structure:

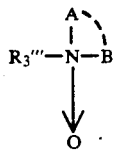

with other materials, the upper bound of the temperature range is the decomposition point of any one of the diphenyl oxide derivatives or amine oxide components and the lower bound is the least temperature where a single liquid phase or gel phase, including the diphenyl oxide derivatives or diphenyl oxide-amine oxide mixture will exist.

Preferred diphenyl oxide derivative compositions from a practical standpoint useful in the practice of our invention are compounds having the structure:

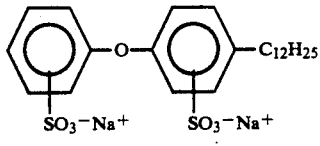

where the $C_{12}H_{25}$ moiety represents one or a series of different branched chains; compounds defined according to the structure:

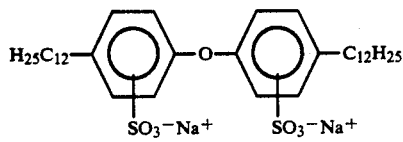

where the $C_{12}H_{25}$ moiety represents one or a series of different branched chains; compounds defined according to the structure:

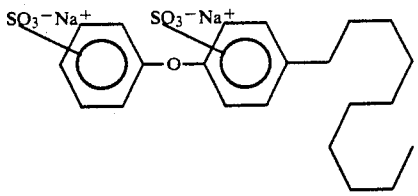

and compounds defined according to the structure:

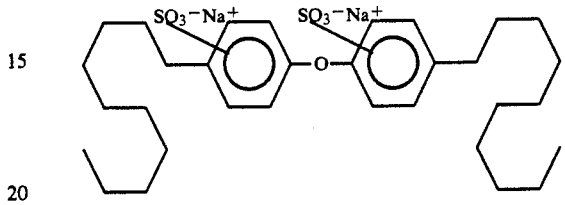

otherwise known as DOWFAX® 1A1 in the case where one of $R_1$ or $R_2$ represents branched $C_{12}H_{25}$ alkyl chains and the other of $R_1$ or $R_2$ represents hydrogen, or DOWFAX® 3B2 in the case where one of $R_1$ or $R_2$ represents hydrogen (DOWFAX® being a registered trademark of the Dow Chemical Company of Midland, Mich.)

When used in conjunction with the dipehnyl oxide derivaties preferred amine oxide compositions, from a practical standpoint, useful in the practice of our invention are the commercially available (1) dimethyl "cocoamine" oxide (a mixture which is dominated by dimethyl-$C_{12}$-$C_{16}$ straight chain alkyl amine oxides; more particularly a mixture containing approximately 70% $C_{12}$ straight chain alkyl amines oxides, approximately 25% of straight chain $C_{14}$ alkyl amine oxides and approximately 4% straight chain $C_{16}$ alkyl amine oxides) and (2) N-cocomorpholine oxide, a mixture dominated by straight chain $C_{12}$-$C_{16}$ alkyl morpholine oxides (specifically containing approximately 70% straight chain $C_{12}$ alkyl morpholine oxide, approximately 25% straight chain $C_{14}$ alkyl morpholine oxide, and approximately 4% straight chain $C_{16}$ alkyl morpholine oxide). Commercial examples of such amine oxide compositions are: AROMO® DMC-W and AROMOX® DMMC-W which are 30% aqueous dimethyl cocoamine oxide solutions and AROMOX® NCMDW which is a 40% aqueous N-cocomorpholine oxide solution each of which is produced by the Armac Division of AKZO of Chicago, Illinois. These materials are described in Brochure 68011, published by Armour Industrial Chemicals, P.O. Box 1805, Chicago, Ill. 60690. Other preferred amine oxides are n-undecyl dimethyl amine oxide and n-tridecyl dimethyl amine oxide.

The percentage of hypochlorite ion in the compositions of our invention may vary from about 1% up to about 20% for the desired effects to be produced using the diphenyl oxide derivative or diphenyl oxide derivative-amine-oxide 2,2-dimethyl-4-phenyl valeronitrile compositions covered by our invention. The usual percent of alkali metal hypochlorite in solution is about 5%, t age of sodium hypochlorite in such mixtures as CLOROX® the registered trademark of the Clorox Corporation.

The perfume oil used in conjunction with the 2,2-dimethyl-4-phenyl valeronitrile which, in turn, is used in conjunction with the aqueous alkali metal hypochlorite solution must have such properties as to be able (1) to be compatible with the 2,2-dimethyl-4-phenyl valeronitrile; (2) to impart to the resulting or "aqueous alkali metal hypochlorite" liquid or gel solution a pleasant aroma which harmonizes with the aroma of the 2,2-dimethyl-4-phenyl valeronitrile; (3) to effect a substantial diminution or elimination of the disagreeable "hypochlorite" aroma which is imparted to surfaces (e.g., bleached laundry or the hands of the user which are in direct contact with the hypochlorite solution) on which known aqueous alkali metal hypochlorite solutions have been used: and (4) to impart to the surfaces with which such aqueous alkali metal hypochlorite solutions are in contact, a pleasant long lasting stable aroma. Examples of ingredients compatible with 2,2-dimethyl-4-phenyl valeronitrile and suitable for the aforementioned purposes, that is, useable in conjunction with the hypochlorites, amine oxide derivatives and diphenyl oxide derivatives of our invention are as follows:

1. Cedryl alkyl ethers covered by U.S. Pat. No. 3,373,208 such as cedryl methyl ether;
2. Isochroman musks covered by U.S. Pat. No. 3,360,530 and 3,591,528 such as 6-oxa-1,1,3,3,8-pentamethyl-2,3,5,6,7,8-hexahydro-1 H-benz(f)indene;
3. Polycyclic ethers covered by U.S. Pat. No. 3,281,432, such as octahydro-1,3a,6-trimethyl-1 H-1,6a,ethanopentaleno-(1,2-C)furan;
4. Polycyclic ketones such as hexahydro-1,1,5,5-tetramethyl-2H-2,4a-methanonaphthalen-8-(5H)one;
5. Diisoamylenes described according to application for U.S. Letters Pat., Ser. No. 188,576 filed on Sep. 18, 1980;
6. Acyl diisoamylene derivatives described according to application for U.S. Letters Pat., Ser. No. 184,132 filed on Sep. 4,1980 and ketal derivatives thereof described according to application for U.S. Letters Pat., Ser. No. 212,993 filed on Dec. 4, 1980; and
7. Diisoamylene epoxide derivatives prepared according to application for U.S. Letters Pat., Ser. No. 231,773 filed on Feb. 27, 1981.

It will be understood that a number of materials which impart to the vetivert, peppery, grapefruit and Bergamot aroma of the 2,2-dimethyl-4-phenyl valeronitrile of our invention additional eucalyptol or minty or woody nuances will not be useful for this aspect of our invention because they are, interalia, easily oxidized by the alkali metal hypochlorite in the system. Examples are 1,5,9-trimethyl-12 TM acetyl-cyclo-dodecatriene-1,5,8 and 1,5,9-trimethyl-12-cyclododec covered by British Patent No. 1,204,409.

A basic feature of our invention concerns the fact that the only detergent group needed or desirable in the composition of our invention is the class of diphenyl oxide derivatives defined according to the structure:

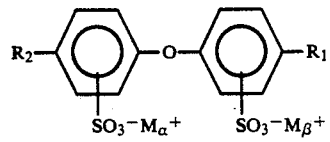

wherein $R_1$, $R_2$, $M_\alpha$ and $M_\beta$ are defined, supra, taken alone or in conjunction with the class of morpholino and/or dimethyl $C_{11}$–$C_{13}$ straight chain alkyl amine oxides defined according to the structure:

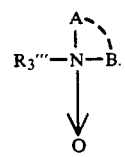

More specifically, such detergents as sodium decyl ether sulfate, sodium myristyl ether sulfate, sodium lauryl ether sulfate and lithium lauryl ether sulfate are neither desired nor are they required. Furthermore, the well known hydrotropes employed in prior art compositions such as the well known family of clarifying agents comprising the alkali metal or alkali earth metal salts of mono- and polyalkylated benzene or naphthalene sulfonates such as sodium xylene or magnesium toluene sulfonate are again neither desired nor are they required in the compositions intended to be encompassed by the instant invention.

Another basic feature of our invention concerns the fact that when it is desired to have a gel phase composition, thickener agents may be employed in conjunction with the system; hypochlorite bleach-2,2-dimethyl-4-phenyl valeronitrile-diphenyl oxide derivative or diphenyl oxide derivative-amine oxide derivative (having the general structure

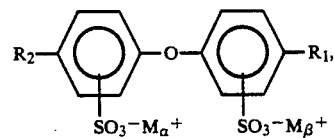

and having the structure:

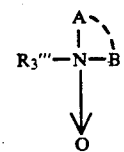

of our invention).

Still another basic feature of our invention concerns the fact that the gel phase compositions including thickener agents are employed with the "premix" system: 2,2-dimethyl-4-phenyl valeronitrile-diphenyl oxide derivative or diphenyl oxide derivative-amine oxide of our invention.

Thus, sodium palmitate, sodium stearate, sodium laurate, potassium palmitate, potassium stearate, potassium laurate, lithium palmitate, lithium stearate and/or lithium laurate or combinations of the foregoing may be added to the compositions of matter of our invention to provide a thickened gel-type hypochlorite bleach which is, in addition to being in a semi-solid state, is unobviously, advantageously and unexpectedly stable over long periods of time. Percentages of thickening agents such as sodium palmitate, sodium stearate, sodium laurate, potassium palmitate, potassium stearate, potassium laurate, lithium palmitate, lithium stearate or lithium laurate or combinations of these which may be used in the thickened compositions of our invention are from 1% by weight up to 12% by weight of the thickener based on the overall weight of hypochlorite bleach-diphenyl oxide derivative (or diphenyl oxide derivative-amine oxide)-2,2-dimethyl-4-phenyl valeronitrile composition of our invention. When it is merely desired to have a thickened "premix" the percentage of thickening agent may vary from about 5% up to about 40% by weight of thickener based on overall weight of "premix".

The following Examples I, II and III serve to illustrate process of our invention. Example III illustrates a process for preparing the 2,2-dimethyl-4-phenyl valeronitrile of our invention for which the novel utilities are claimed. Examples following Example III in general serve to illustrate the organoleptic utilities of the 2,2-dimethyl-4-phenyl aleronitrile of our invention.

In general, the following examples serve to illustrate specific embodiments of our invention. It will be understood that these examples are illustrative and that the invention is to be considered restricted thereto only as indicated in the appended claims.

All parts and percentages given herewith are by weight unless otherwise specified.

EXAMPLE I

2,2-DIMETHYL-4-PHENYL BUTYRONITRILE

Reaction:

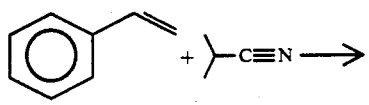

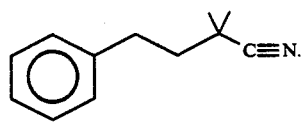

Into a 3 liter reaction flask equipped with stirrer, thermometer, reflux condensr and heating mantle is placed 138 grams (2.0 moles) of isobutyronitrile having the structure:

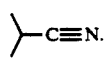

While maintaining the reaction vessel at 22° C., with stirring, over a 20 minute period 4.6 grams (0.2 moles) of sodium is added to the reaction mass. The reaction is exothermic and the temperature is permitted to rise to 38° C. At the end of the feeding of the sodium metal, the reaction mass temperature is heated to 65°–70° C. Over a period of 20 minutes, 104 grams (1.0 moles) of styrene is added to the reaction mass. The reaction mass is then stirred for a period of 2 hours at 90° C.

At the end of the two hour period, no reaction product was formed having the structure:

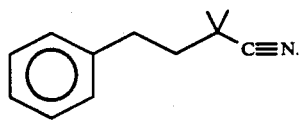

7.5 Grams of sodium hydrode was then added to the reaction mass while maintaining the temperature at 40° C.

The reaction mass was then heated to reflux and the reaction mass was refluxed for a period of eight hours at 100° C.

At the end of the eight hour period, GLC, NMR and IR analyses yield the information that the product having the structure:

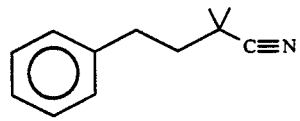

was formed in a yield of 74%.

EXAMPLE II PREPARATION OF

2,2-DIMETHYL-4-(4'-METHYLPHENYL) BUTYRONITRILE

Reaction:

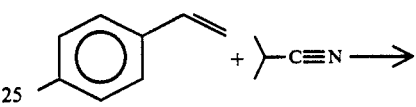

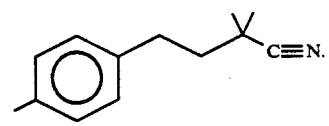

Into a 2 liter reaction flask equipped with stirrer, thermometer, reflux condenser and heating mantle is placed 138 grams (2.0 moles) of isobutyronitrile having the structure:

Over a fifteen minute period, 4.6 grams (0.2 moles) of sodium metal is added to the reaction mass. The reaction mass exotherms to 50° C. At the end of the sodium addition, over a period of ten minutes while maintaining the reaction mass at 38°–40° C., 122 grams (1.0 moles) of the compound having the structure:

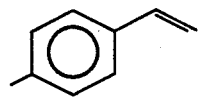

is added to the reaction mass. The reaction mass is then heated to reflux and maintained at reflux for a period of two hours (105°–110° C.). At the end of the two hour period, no reaction has occurred whereby the product:

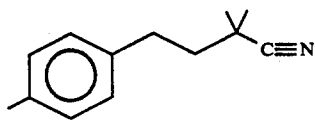

is formed. The reaction mass is then cooled.

Over a period of five minutes while maintaining the reaction mass at 40° C., 7.5 grams (0.25 moles) of 80% sodium hydride is added to the reaction mass. The reaction mass is then refluxed at 110° C. for a period of nine hours.

At the end of the nine hour period, the reaction mass is cooled and 500 ml water is added to the reaction mass. The reaction mass is then acidified with concentrated hydrochloric acid (30 ml). The organic phase is washed with 400 ml of 10% sodium bicarbonate followed by two 300 ml portions of saturated sodium chlorite. The reaction mass is then filtered through CELITE ® and fractionally distilled yielding the compound having the structure:

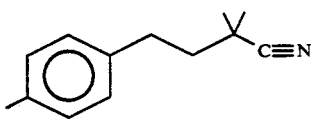

(confirmed by NMR and IR analyses)(yield: 65%)

EXAMPLE III

PREPARATION OF 2,2-DIMETHYL-4-PHENYL VALERONITRILE

Reaction:

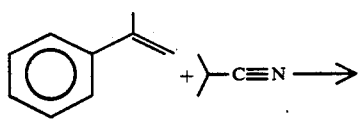

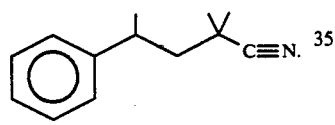

Into a 5 liter reaction flask equipped with stirrer, thermometer, reflux condenser and heating mantle are placed 414 grams (6 moles) of isobutyronitrile having the structure:

and 24 grams (0.8 moles) of an 80% suspension of sodium hydride. With stirring, while maintaining the reaction mass at a temperature of 24° C., over a ten minute period, 472 grams (4 moles) of the compound having the structure:

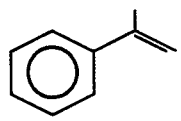

is added to the reaction mass.

The reaction mass is then refluxed at a temperature of 110°-114° C. for a period of thirteen hours.

At the end of the thirteen hour period, an additional 12 grams (0.4 moles) of sodium hydride and 138 grams (2 moles) of isobutyronitrile is added to the reaction mass. The reaction mass is then refluxed for another period of thirteen hours at 118° C.

An additional 12 grams (0.4 moles) of sodium hydride is then added to the reaction mass. The reaction mass is then refluxed at 120° C. for a period of six hours.

The reaction mass is then cooled to 25° C. and 300 ml of 30% aqueous hydrochloric acid is added to the reaction mass.

600 ml Toluene is then added to the reaction mass and the resulting product is then filtered through CELITE ®.

The reaction mass now exists in two phases; an organic phase and an aqueous phase The organic phase is separated from the aqueous phase and the organic phase is washed with 300 ml 30% hydrochloric acid followed by 400 ml 10% sodium bicarbonate followed by 300 ml saturated sodium chloride solution.

The resulting product is then filtered through anhydrous magnesium sulfate/CELITE ®.

The resulting product is fractionally distilled yielding 88% product having the structure:

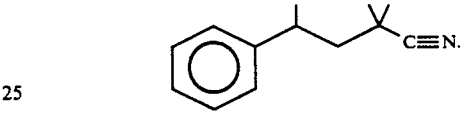

The distillation conditions are as follows:

| Fraction No. | Vapor Temp. (°C.) | Liquid Temp. (°C.) | Vacuum mm/Hg. Pressure |
|---|---|---|---|
| 1 | 42/65 | 57/105 | 1.50/2.53 |
| 2 | 90 | 108 | 4.49 |
| 3 | 95 | 113 | 2.48 |
| 4 | 96 | 115 | 2.44 |
| 5 | 98 | 116 | 2.44 |
| 6 | 98 | 118 | 2.43 |
| 7 | 98 | 121 | 2.40 |
| 8 | 98 | 138 | 2.42 |
| 9 | 90 | 200 | 2.61 |

Fractions 3-7 are bulked.

Bulked distillation fractions 3-7 have a vetivert, peppery, grapefruit and Bergamot aroma profile, with vetivert, peppery and Bergamot topnotes.

FIG. 1 is the GLC profile of the crude reaction product prior to distillation. (Conditions: Carbowax column programmed at 220° C. isothermal).

The peak indicated by reference numeral 10 is the peak for the starting material, the isobutyronitrile having the structure:

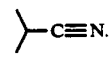

The peak indicated by reference numeral 12 is the peak for the compound having the structure:

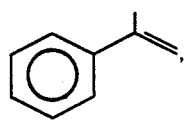

a starting material. The peak indicated by reference numeral 14 is the peak for the compound having the structure:

FIG. 2 is the NMR spectrum for the compound having the structure:

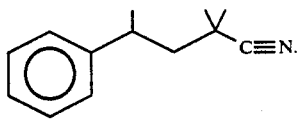

FIG. 3 is the infra-red spectrum for the compound having the structure:

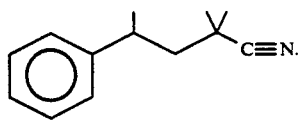

EXAMPLE IV

The following Chypre formulation is prepared:

| Ingredients | Parts by Weight |
| --- | --- |
| Musk ambrette | 40 |
| Musk ketone | 60 |
| Coumarin | 30 |
| Oil of bergamot | 150 |
| Oil of lemon | 100 |
| Methyl ionone | 50 |
| Hexyl cinnamic aldehyde | 100 |
| Hydroxycitronellal | 100 |
| Oil of lavender | 50 |
| Texas cedarwood oil | 85 |
| Virginia cedarwood oil | 30 |
| Oil of sandalwood (East Indies) | 40 |
| Eugenol | 10 |
| Benzyl acetate | 30 |
| alpha-Phenyl ethyl alcohol | 40 |
| beta-Phenyl ethyl alcohol | 30 |
| Oakmoss absolute | 30 |
| Vetiver oil Venezuela | 25 |
| The compound having the structure: 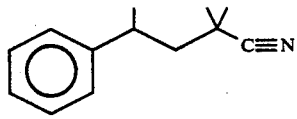 prepared according to Example III, bulked distillation fractions 3-7. | 62 |

The compound having the structure:

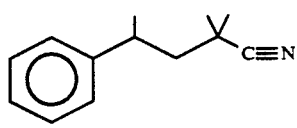

prepared according to Example III, imparts to this Chypre formulation vetivert, peppery, grapefruit and Bergamot undertones, with vetivert, peppery and Bergamot topnotes. Accordingly, the Chypre formulation prepared above can be described as follows "Chypre, with vetivert, peppery, grapefruit and Bergamot undertones and vetivert, peppery and Bergamot topnotes".

EXAMPLE V

PREPARATION OF COSMETIC POWDER COMPOSITIONS

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| Substance | Aroma Description |
| --- | --- |
| The compound having the structure: 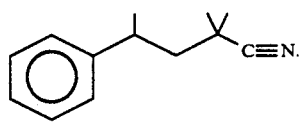 prepared according to Example III, bulked distillation fractions 3-7. | A vetivert, peppery, grapefruit and Bergamot aroma, with vetivert, peppery and Bergamot topnotes. |
| Perfume composition of Example III. | Chypre, with vetivert, peppery, grapefruit and Bergamot undertones and vetivert, peppery and Bergamot topnotes |

EXAMPLE VI

PERFUMED LIQUID DETERGENTS

Concentrated liquid detergents (Lysine salt of n-dodecylbenzene sulfonic acid as more specifically described in U.S. Pat. No. 3,948,818 issued on Apr. 6, 1976) with aroma nuances as set forth in Table II of Example V are prepared containing 0 10%, 0.15%, 0.20%, 0.25%, 0.30% and 0.35% of the substance set forth in Table II of Example V They are prepared by adding and homogeneously mixing the appropriate quantity of substance set forth in Table II of Example V in the liquid detergent. The detergents all possess excellent aromas as set forth in Table II of Example V, the intensity increasing with greater concentrations of substance as set forth in Table II of Example V.

EXAMPLE VII

PREPARATION OF COLOGNES AND HANDKERCHIEF PERFUMES

Compositions as set forth in Table II of Example V are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example V are imparted to the colognes and to the handkerchief perfumes at all levels indicated.

EXAMPLE VIII

PREPARATION OF SOAP COMPOSITIONS

One hundred grams of soap chips [per sample]-(IVORY ®, produced by the Procter & Gamble Company of Cincinnati, Ohio), are each mixed with one gram samples of substances as set forth in Table II of Example V until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table II of Example V.

EXAMPLE IX

PREPARATION OF SOLID DETERGENT COMPOSITIONS

Detergents are prepared using the following ingredients according to Example I of Canadian Patent No 1,007,948:

| Ingredient | Percent by Weight |
|---|---|
| "NEODOL ® 45-11 (a $C_{14}$-$C_{15}$ alcohol ethoxylated with 11 moles of ethylene oxide | 12 |
| Sodium carbonate | 55 |
| Sodium citrate | 20 |
| Sodium sulfate, water brighteners. | q.s. |

This detergent is a phosphate-free detergent. Samples of grams each of this detergent are admixed with 0.10, 0.15, 0.20 and 0.25 grams of each of the substances as set forth in Table II of Example V. Each of the detergent samples has an excellent aroma as indicated in Table II of Example V.

EXAMPLE X

Utilizing the procedure of Example I at column 15 of U.S. Pat. No. 3,632,396, non-woven cloth substrates useful as drier-added fabric softening articles of manufacture are prepared wherein the substrate, the substrate coating and the outer coating and the perfuming material are as follows:

1. A water "dissolvable" paper ("Dissolve Paper");
2. Adogen 448 (m.p. about 140° F.) as the substrate coating; and
3. An outer coating having the following formulation (m.p. about 150° F.):
   57% —C20—22 HAPS
   22% —isopropyl alcohol
   20% —antistatic agent
   1% —of one of the substances as set forth in Table II of Example V.

Fabric softening compositions prepared according to Example I at column 15 of U.S. Pat. No. 3,632,396 having aroma characteristics as set forth in Table II of Example V, consist of a substrate coating having a weight of about 3 grams per 100 square inches of substrate; a first coating on the substrate coating consisting of about 1.85 grams per 100 square inches of substrate; and an outer coating coated on the first coating consisting of about 1.4 grams per 100 square inches of substrate. One of the substances of Table II of Example V is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said dryer-added fabric softener non-woven fabrics and these aroma characteristics are described in Table II of Example V.

EXAMPLE XI

HAIR SPRAY FORMULATIONS

The following hair spray formulation is prepared by first dissolving PVP/VA E-735 copolymer manufactured by the GAF Corporation of 140 West 51st Street, New York, N.Y., in 91.62 grams of 95% food grade ethanol, 8.0 grams of the polymer is dissolved in the alcohol. The following ingredients are added to the PVP/VA alcoholic solution:

| Ingredients | Weight Percent |
|---|---|
| Dioctyl sebacate | 0.05 |
| Benzyl alcohol | 0.10 |
| Dow Corning 473 fluid (prepared by the Dow Corning Corporation) | 0.10 |
| Tween 20 surfactant (prepared by ICI America Corporation) | 0.03 |
| One of the perfumery substances as set forth in Table II of Example V. | 0.10 |

The perfuming substances as set forth in Table II of Example V add aroma characteristics as set forth in Table II of Example V which are rather intense and aesthetically pleasing to the users of the soft-feel, good hold pump hair sprays.

EXAMPLE XII

CONDITIONING SHAMPOOS

Monamid CMA (prepared by the Mona Industries Company)(3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation)(1.4 weight percent). The resulting melt is admixed with Stepanol WAT produced by the Stepan Chemical Company (35.0 weight percent). The resulting mixture is heated to 60° C. and mixed until a clear solution is obtained (at 60° C.).

GAFQUAT ® 755N polymer (manufactured by GAF Corporation of 140 West 51st Street, New York, New York)(5.0 weight percent) is admixed with 0.1 weight percent sodium sulfite and 1.4 weight percent polyethylene glycol 6000 distearate produced by Armak Corporation.

The resulting material is then mixed and cooled to 45° C. and 0.3 weight percent of perfuming substance as set forth in Table II of Example V is added to the mixture The resulting mixture is cooled to 40° C. and blending is carried out for an additional one hour in each case. At the end of this blending period, the resulting material has a pleasant fragrance as indicated in Table II of Example V.

EXAMPLE XIII Four drops of each of the substances set forth in Table II of Example V, supra, is added separately to two grams of AROMOX ® to produce a clear premix. The clear premix is added to 200 grams of CLOROX ® with stirring resulting in a clear stable, single phase solution Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry, on dry-out in an atmosphere of 65% relative humidity yields substantially no characteristic "hypochlorite" odor, but does have a faint pleasant aroma as set forth in Table II of Example V. Furthermore, no such characteristic "hypochlorite" aroma is retained on the hands of the individual handling such laundry in both the wet and the dry states.

EXAMPLE XIV

AROMOX ® DMMC-W in various quantities is mixed with 0.1 grams of one of the substances set forth in Table II of Example V, supra. The resulting premixes are then added to 200 grams of an aqueous 5% sodium hypochlorite solution. Sufficient 12.5M aqueous NaOH is added to bring the pH of the mixture up to 13. The following results are obtained:

| Percentage AROMOX ® DMMC-W | Clarity of hypochlorite solution after addition of premix |
|---|---|
| 0.23% | Clear after three days |
| 0.15% | Clear after three days |
| 0.08% | Initially slightly turbid; two phases exist after three days. |

When the 5% aqueous sodium hypochlorite solution is used as a laundry bleach, the resulting laundry on dry-out, in an atmosphere of 65% relative humidity, yields substantially no characteristic "hypochlorite" odor, but does have a faint, pleasant aroma as set forth in Table II of Example V. Furthermore, no such characteristic "hypochlorite" aroma is retained on the hands of the individual handling such laundry in both the wet and dry states.

EXAMPLE XV

Two grams of AROMO ® DMMC-W is admixed with eight drops of one of the substances set forth in Table II of Example V, supra. The premix is then added with stirring to 200 grams of a 7% aqueous solution of lithium hypochlorite. Sufficient 3M aqueous LiOH is added to bring the pH of the solution to 13.4. The mixture is then heated to 120° F. and maintained at that temperature with stirring for a period of one week. The resulting solution remains clear in a single phase When used as a laundry bleach, the resulting bleached laundry, on dry-out in an atmosphere of 50% relative humidity retains a "clean" warm aroma as set forth in Table II of Example V, supra; whereas without the use of the substance set forth in Table II of Example V, supra, the bleached laundry has a faint characteristic disagreeable "hypochlorite" aroma.

EXAMPLE XVI

Two grams of AROMOX ® DMMC-W is admixed with eight drops of one of the substances of Table II of Example V, supra. This premix is then added, with stirring to 200 grams of a mixture containing 4.5% aqueous sodium hypochorite. Sufficient 4M aqueous LiOH is added to bring the pH of the solution to 13.4. The mixture is then heated to 120° F. and maintained at that temperature for a period of one week The resulting solution remains clear in a single phase. When used as a laundry bleach, the resulting bleached laundry on dry-out in an atmosphere of 50% relative humidity retains a "clean fresh" warm aroma as set forth in Table II of Example V, supra; whereas without the use of the substance set forth in Table II of Example V, supra, the bleached laundry has a faint characteristic disagreeable "hypochlorite" aroma.

EXAMPLE XVII

Two grams of AROMOX ® DMMC-W is admixed with eight drops of one of the substances as set forth in Table II of Example V, supra. This premix is then added with stirring to 200 grams of a mixture containing 4.5% aqueous sodium hypochlorite and 4.5% aqueous lithium hypochlorite. Sufficient 2M aqueous NaOH is added to bring the pH of the solution to 13.4. The mixture is then heated to 110° F. and maintained at that temperature with stirring for a period of 2 weeks. The resulting solution remains clear as a single phase when used as a laundry bleach. The resulting laundry bleach, on dry-out in an atmosphere of 50% relative humidity, retains an aroma as set forth in Table II of Example V, supra, whereas without the use of the substance set forth in Table II of Example V, supra, the bleached laundry has a faint characteristic disagreeable "hypochlorite" aroma.

EXAMPLE XVIII

Four drops of one of the substances set forth in Table II of Example V, supra, is added to 1.5 grams of AROMOX ® to produce a clear premix. The clear premix is added to 200 grams of CLOROX ® with stirring resulting in a clear stable single phase solution. Sufficient 1M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant warm, long-lasting aroma as set forth in Table II of Example V, supra. Furthermore, no such characteristic "hypochlorite" aroma is retained on the hands of the individual handling such laundry in both the wet and dry states.

EXAMPLE XIX

Four drops of one of the substances set forth in Table II of Example V, supra, is added to 1 gram n-undecyl dimethyl amine oxide to produce a clear premix. The clear premix is added to 200 grams of CLOROX ® with stirring resulting in a clear stable single phase solution Sufficient 1M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant warm aroma as set forth in Table II of Example V, supra. Furthermore, no such characteristic "hypochlorite" aroma is retained on the hands of the individual handling such laundry in both the wet and the dry states.

EXAMPLE XX

Four drops of one of the substances as set forth in Table II of Example V, supra are added to 1 gram of n-dodecyl dimethyl amine oxide to produce a clear premix. The clear premix is added to 200 grams of CLOROX ® with stirring resulting in a clear, stable single phase solution. Sufficient 1M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" aroma, but does have a warm, pleasant, long-lasting aroma as set forth in Table II of Example V, supra. Furthermore, no such characteristic "hypochlorite" aroma is retained on the hands of the individual handling such laundry in both the wet and dry states.

EXAMPLE XXI

One gram of n-tridecyl dimethyl amine oxide is admixed with eight drops of one of the substances as set forth in Table II of Example V, supra This premix is then added with stirring to 200 grams of a 7% aqueous solution of lithium hypochlorite. Sufficient 3M aqueous LiOH is added to bring the pH of the solution to 13.4. The mixture is then heated to 120° F. and maintained at that temperature with stirring for a period of one week The resulting solution remains clear in a single phase. When used as a laundry bleach, the resulting bleached laundry on dry-out in an atmosphere of 50% relative humidity retains the aroma having the nuances described in Table II of Example V, supra, whereas without the use of one of the substances of Table II of Example V, supra, the bleached laundry has a faint characteristic disagreeable "hypochlorite" aroma.

EXAMPLE XXII

Four drops of the compound having the structure:

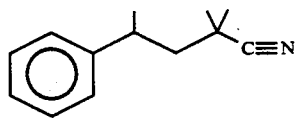

prepared according to Example III (bulked distillation fractions 3-7) is added to 2 grams of AROMOX ® DMC-W to produce a premix. The clear premix is added to 200 grams of CLOROX ® with stirring resulting in a clear stable single phase solution Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor but does have a strong fresh substantive vetivert, peppery, grapefruit and Bergamot aroma profile, with vetivert, peppery and Bergamot topnotes. Furthermore, no such characteristic "hypochlorite" aroma is retained on the hands of the individual handling such laundry in both the wet and the dry states.

EXAMPLE XXIII

AROMO ® DMMC-W in various quantities is mixed with 0.1 grams of the compound having the structure:

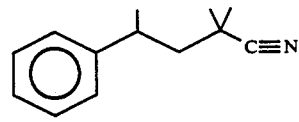

prepared according to Example III (bulked fractions 3-7). The resulting premix is then added to 200 grams of an aqueous 5% sodium hypochlorite solution. Sufficient 12.5M aqueous NaOH is added to bring the pH of the mixture up to 13. The following results are obtained:

| Percentage AROMOX ® DMMC-W | Clarity of Hypochlorite Solution After Addition of Premix |
| --- | --- |
| 0.23% | Clear after three days. |
| 0.15% | Clear after three days. |
| 0.08% | Initially slightly turbid; two phases exist after three days. |

When the 5% aqueous sodium hypochlorite solutions are used as laundry bleaches, the resulting laundry batches on dry-out in an atmosphere of 65% relative humidity yields substantially no characteristic "hypochlorite" odor, but does have a strong fresh, warm vetivert, peppery, grapefruit and Bergamot aroma profile, with vetivert, peppery and Bergamot topnotes. Furthermore, no such characteristic "hypochlorite" aroma is retained on the hands of the individual handling such laundry batches in both the wet and the dry states.

EXAMPLE XXIV

Two grams of AROMOX ® DMMC-W are admixed with eight drops of the compound having the structure:

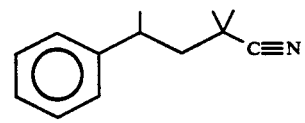

prepared according to Example III (bulked fractions 3-7). The premix is then added with stirring to 200 grams of a 7% aqueous solution of lithium hypochlorite. Sufficient 3M aqueous LiOH is added to bring the pH of the solution to 13.4. The mixtures are then heated to 120° F. and maintained at that temperature with stirring for a period of one week. The resulting solution remains clear in a single phase. When used as laundry bleaches, the resulting bleached laundry batches on dry-out in an atmosphere of 50% relative humidity retain a strong, fresh, warm vetivert, peppery, grapefruit and Bergamot aroma, with vetivert, peppery and Bergamot topnotes whereas without the use of the compound having the structure:

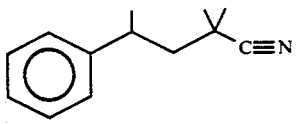

prepared according to Example III (bulked fractions 3-7), the bleached laundry batches have a faint characteristic disagreeable "hypochlorite" aroma.

EXAMPLE XXV

Two grams of AROMO ® DMMC-W are admixed with eight drops of the compound having the structure:

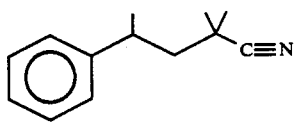

prepared according to Example III (bulked fractions 3-7). The premix is then added with stirring to 200 grams of a mixture containing 4.5% aqueous sodium hypochlorite and 4.5% aqueous lithium hypochlorite. Sufficient 4M aqueous LiOH is added to bring the pH of the solution to 13.4. The mixture is then heated to 120° F. and maintained at that temperature for a period of one week. The resulting solution remains clear in a single phase. When used as a laundry bleach, the resulting bleached laundry batches on dry-out in an atmosphere of 50% relative humidity retain a strong fresh warm vetivert, peppery, grapefruit and Bergamot aroma, with vetivert, peppery and Bergamot topnotes whereas without the use of the compound having the structure:

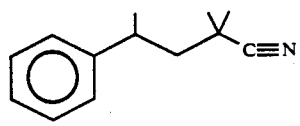

prepared according to Example III (bulked fractions 3-7), the bleached laundry batches have faint characteristic disagreeable "hypochlorite" aroma.

What is claimed is:

1. A process for preparing a phenyl butyronitrile defined according to the structure:

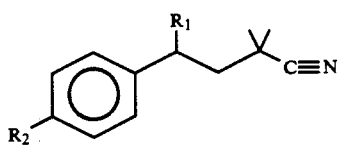

wherein $R_1$ and $R_2$ are the same or different and each represents hydrogen or methyl comprising the step of intimately admixing a compound having the structure:

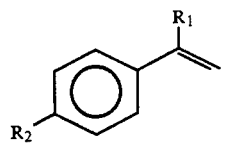

with isobutyronitrile having the structure:

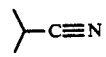

in the presence of a catalyst selected from the group consisting of sodium hydride and lithium diisopropyl amide having the structure:

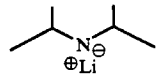

at a temperature in the range of from about 90° C. up to about 130° C. for a period of time such that the compound having the structure:

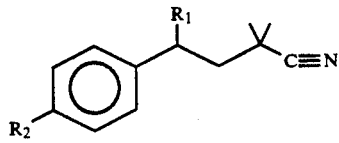

is produced in a yield in excess of about 65% according to the reaction:

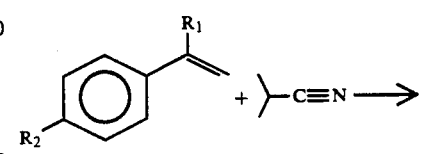

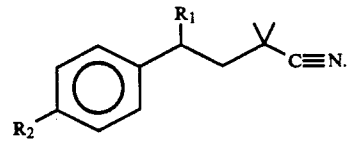

2. The process of claim 1 wherein $R_1$ is methyl and $R_2$ is hydrogen.

3. The process of claim 1 wherein $R_1$ is hydrogen and $R_2$ is hydrogen.

4. The process of claim 1 wherein $R_1$ is hydrogen and $R_2$ is methyl.

* * * * *